United States Patent [19]
Sampson

[11] Patent Number: 5,098,403
[45] Date of Patent: Mar. 24, 1992

[54] UNIVERSAL NEEDLE GUARD

[75] Inventor: Edward J. Sampson, Carlisle, Mass.

[73] Assignee: Infusaid Inc., Norwood, Mass.

[21] Appl. No.: 446,343

[22] Filed: Dec. 5, 1989

[51] Int. Cl.$^5$ .............................................. A61M 5/32
[52] U.S. Cl. .................................... 604/198; 604/263
[58] Field of Search ............... 604/192, 198, 187, 263, 604/164

[56] References Cited

U.S. PATENT DOCUMENTS

| | | | |
|---|---|---|---|
| 4,631,057 | 12/1986 | Mitchell | 604/198 |
| 4,695,274 | 9/1987 | Fox | 604/198 |
| 4,743,233 | 5/1988 | Schneider | 604/192 |
| 4,758,231 | 7/1988 | Haber et al. | 604/198 |
| 4,819,659 | 4/1989 | Sitar | 604/198 |
| 4,832,696 | 5/1989 | Luther et al. | 604/192 X |
| 5,011,479 | 4/1991 | Le et al. | 604/263 X |

*Primary Examiner*—John D. Yasko
*Attorney, Agent, or Firm*—Sughrue, Mion, Zinn, Macpeak & Seas

[57] ABSTRACT

A needle guard attachment for a syringe. The guard has a pair of concentric members one of which establishes fluid communication between the needle and the syringe body. The other member slides to cover the needle. Once in an extended position it locks into place to act as a sheath over the needle. The guard attaches to the needle and the syringe body by luers compatible to those already on the elements.

12 Claims, 2 Drawing Sheets

UNIVERSAL NEEDLE GUARD

BACKGROUND OF THE INVENTION

This invention relates to a syringe and, in particular, to an attachment therefor to prevent needle sticks.

The problem of needle sticks is well known as are a number of proposed solutions. Generally, syringe needles are packaged with a disposable removable sheath. The sheath is removed from the needle when the ringe is used and it may be discarded or lost. Hence, after use the syringe needle remains exposed. In addition to having exposed needles, the problem of recapping the needle is one which leads to the danger of self-inflicted needle wounds with contaminated needles. These sticks include scratches or wounds to members of a health care team or, even individuals who are handling trash.

Thus, a number of devices such as large "needle disposal boxes" are now being used to allow for needles and syringes to be discarded. Those devices are generally inconvenient and expensive. In many facilities needle boxes are either not available or are ignored.

In the case of capping syringes with integral devices, a number of proposals have been made to modify a syringe body to include an attached sheath and needle. Representative are U.S. Pat. Nos. 3,891,971; 4,425,120; and 4,723,943. In each, a syringe body has been modified to include a sheath which slides annularly over the syringe body by means of screw couplings, nobs, detents, latches, guide slots and the like. The sheath is allowed to slide over the needle and prevent sticks. A difficulty with all of these proposals is the expense involved and problems of use. Syringe bodies and needles are used by the millions and thus, proposals which significantly increase their cost are not generally effective. With the overall cost of health care rising such proposals have not found Wide spread utilization. Additionally, syringes are of several different sizes as are the needles which are used with them. Thus, a syringe body may not in some cases have a sheath which matches the length of the needle, it may be too long or too short. Also, many of these proposals add bulk to the syringe making it difficult to use.

Given these deficiencies in the art and with the problem of contamination a serious problem in health care facilities, it is an object of this invention to provide for an improved needle guard.

Yet another object of this invention is to provide for an attachment which may be used with standard, over-the-counter hypodermic needles to prevent accidental needle sticks with a used and contaminated needle.

Another object of this invention is to provide for an attachment that can be used on any syringe and that provides universal protection for the needle to be attached.

SUMMARY OF THE INVENTION

These and other objects of this invention are attained by use of an attachment for a standard syringe. It is made up of two plastic parts, concentric with each other. When retracted one is inside the other, in the extended position the outer collar covers the hypodermic needle and can be locked. One end of the attachment has a male luer and the other a female luer making it possible to attach the device to virtually any combination of apparatus used in conjunction with a hypodermic needle. The most common set up is a syringe and a needle with the attachment assembled therebetween. The attachment has a fine passageway having an internal diameter essentially matching the inside diameter of the needle. This provides fluid communication between the attached needle on one end and the syringe body on the other.

Using this system, after the needle has been used as intended in combination with the syringe body and while it is still exposed the guard is gripped at an annular ridge and the guard is then drawn over the needle. The guard snaps into a locking groove on the inner part and thus cannot ever be retracted to expose the needle again. With the guard over the used/contaminated needle the syringe and contents may be used for other laboratory purposes and thereafter dissembled for sterilization and reuse or disposal. A stopcock can be introduced between the needle guard and the syringe for further handling of the contents thereof. Importantly, the needle and the guard once detached form an integral unit with the needle tip still protected. This component can be discarded without fear of inadvertent stick by either members of the health care team or by disposal personnel.

This invention will be described in greater detail by referring to the attached drawing and the description of the preferred embodiment that follows.

DESCRIPTION OF THE PREFERRED EMBODIMENT

Figure 1:
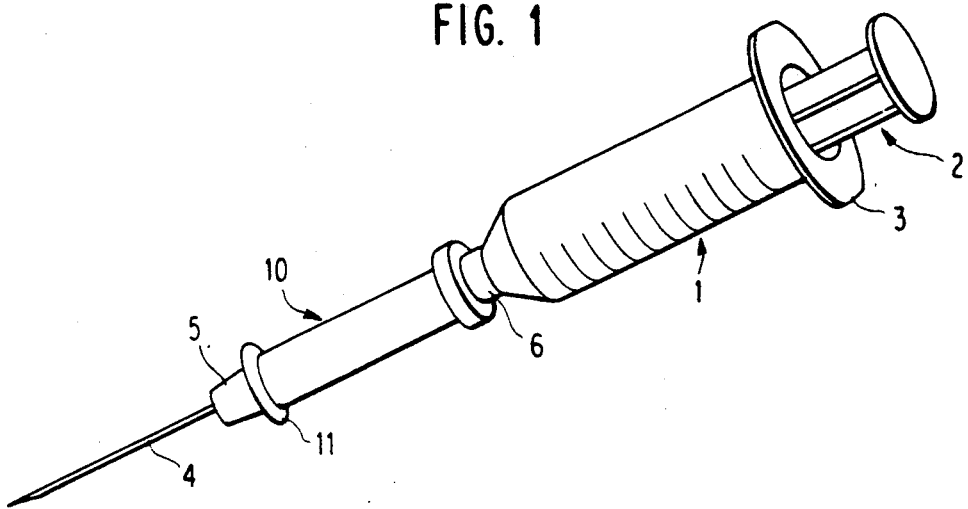
FIG. 1 is a schematic view of a completed unit in accordance with this invention with the needle guard in the retracted position.
Figure 2:
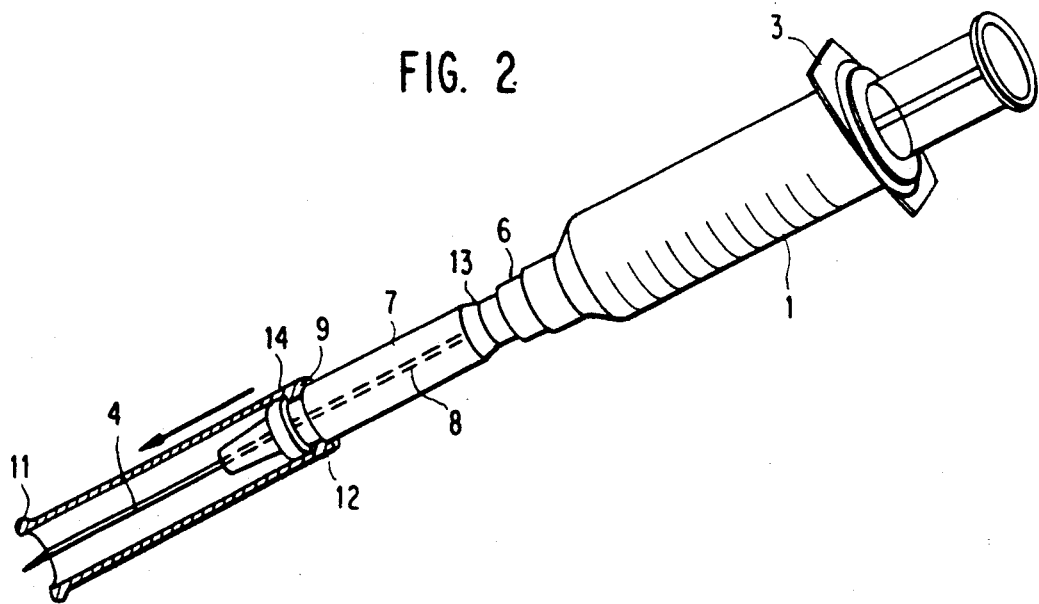
FIG. 2 is a schematic view of the completed assembly of FIG. 1 with the needle guard snapped into its extended position.

Referring now to FIGS. 1 and 2, a preferred embodiment of this invention is depicted. A hollow syringe body 1 with calibrations on the wall has a plunger 2 inserted at one end. Conventionally, the syringe body 1 also has a flange 3 to allow positioning of the fingers to provide the necessary pressure so that the thumb, when resting on the plunger, can press inward.

A needle 4 is also a conventional component. The needle generally has at its proximal end a female luer 5 which attaches to a male luer at the end of the syringe body 1. That is, conventionally the needle attaches to the syringe by means of compatible luer elements. Such is well known in the art to facilitate removal of the needle from the syringe body and replace it with needles of different size or, in the case of glass syringe bodies to replace with new needles after the syringe body has been sterilized.

In accordance with this invention, a universal needle guard is interposed between the syringe body 1 and the needle 4. The needle guard comprises two concentric tubular members, that is, one inside the other. While shown as tubular they may be of any matching cross-section. For example, a triangular section provides flat gripping surfaces. Such would aid in assembly and use.

The inside member 7 has a central through-hole portion 8 with a diameter similar to that of the inside diameter of the needle. This provides fluid communication between the needle 4 and the syringe body 1. It also minimizes the volume so that for purposes of either dosage or fluid sampling, the increased volume requirements of this invention are minimal over those of the needle itself. A circumferential locking groove 9 is provided on the inner body 7 near the distal end.

The outer annular portion comprises a needle guard 10 having a ridge 11 that provides a grip for deployment. One of working skill would recognize that other gripping techniques can be used such as a knurled surface, or other tactile means to indicate the end of the guard. The proximal end of the guard 10 has an inwardly extending annular flange 12. The flange 12 rides over the outer surface of the inner body 7 until it encounters the groove 9. At that point, the flange 12 will snap into the groove by spring pressure fixing the guard over the needle and preventing inadvertent movement.

The inner section of the needle guard attachment 7 has at one end a female luer attachment 13, and at the other end a male luer attachment 14. These two luer attachments are obversely identical to and compatible with those used for the syringe body 1 and the needle 4.

Figure 3A:
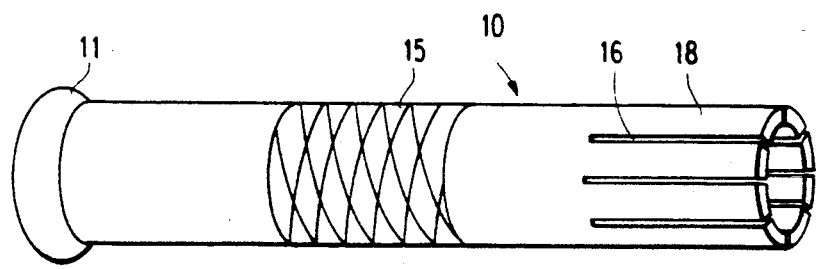
FIG. 3A is a side view of the outer member forming the sheath portion of the needle guard.
Figure 3B:
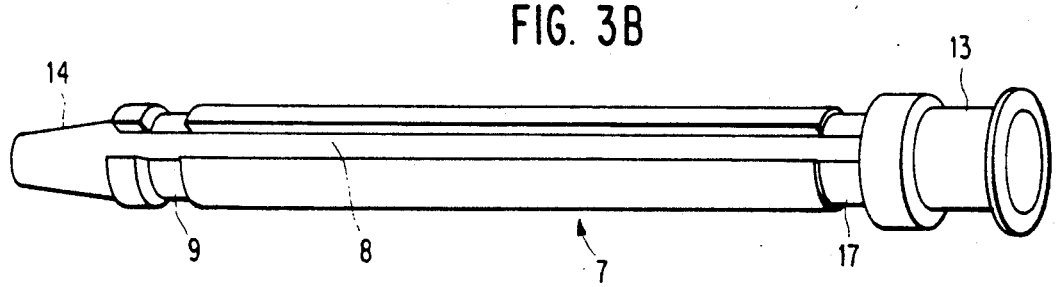
FIG. 3B is a side view of inner member forming the connecting portion for the needle guard.
Figure 3C:
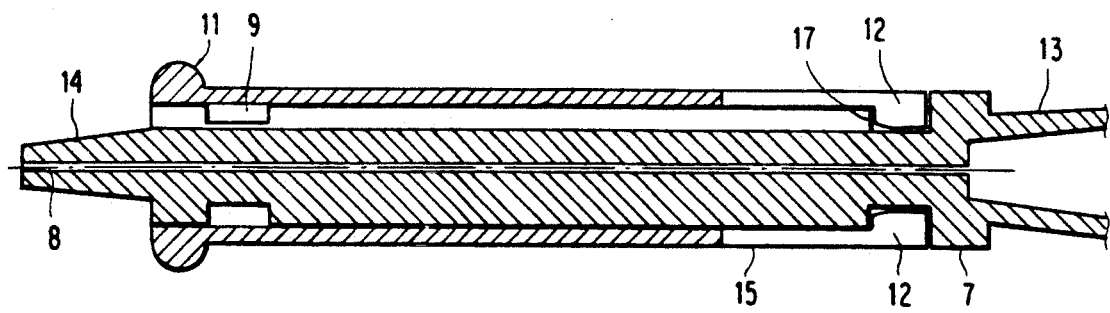
FIG. 3C is a cut-away side view of the assembled needle guard components of FIGS. 3A and 3B.

Referring now to FIGS. 3A, 3B and 3C the details of the needle guard are illustrated. The guard 10 of FIG. 3A has a knurled surface to assist in gripping. The flange 12 comprises a series of snaplock tangs 15 formed by axial slots 16 in the body 10. These provide a degree of spring to allow the flange portion 12 to deflect radially outward on the surface of the inner member 7, see FIG. 3C, yet snap into and lock in the groove 9. As illustrated in FIG. 3B, the attachment portion 7 has a slight annular undercut 17 to receive the snaplock tangs and flanges 12 when the outer member 10 is in the retracted position.

FIG. 3B also illustrates a full length slot 18 into which one flange 12 slides. This slot provides for the transmission of torque to allow the inner section to be twisted on to a syringe, catheter or other medical device at the female luer lock 13. That is, the guard assembly elements 7 and 10 can be held and twisted on to another component with the torque on the outer member 10 transmitted to the inner member 7 by the flange 12 bearing against the sidewall in the slot 18.

The operation of this invention will now be described.

The syringe is assembled by interposing the universal needle guard over the luer on the syringe body and attaching a needle 4 at the opposite end of the guard. The needle is still capped since it has not been used. After using the needle as intended and while it is still "hypodermic" (that is, under the skin) the guard is gripped at the ridge 11. The outer sheath 10 is then drawn over the needle as the needle is withdrawn thereby covering the needle before it is exposed. In this position, as illustrated in FIG. 2 the inner flange 12 snaps into the annular locking groove 9. This prevents the guard from retracting to expose the needle.

Given the fact that the cover 10, as illustrated in FIG. 2, covers the luers mating the needle to the guard, the needle cannot be removed from the needle guard. Rather, only the needle guard and the syringe body may be disassembled. Consequently, the assembly of guard and needle are destroyed in an approved manner without ever exposing the needle point.

As described and illustrated herein then, this invention is applicable wherever needles are used and can be made to securably cover all needle lengths in general use. Additionally it can be applied to any device which is adept to take a needle and will cover that needle as it is withdrawn and before the tip is exposed. This invention thus completely negates the possibility of an accidental needle stick.

It is apparent that modifications of this invention may be practiced without departing from the essential scope thereof. For example, the needle guard would be manufactured using injection molding of known approved medical materials. The needle guard can be made of a colored material to distinguish the guard per se from other components such as the syringe body which is generally transparent.

I claim:

1. An attachment for a syringe body and a needle, comprising:

a pair of concentric members movable axially relative to each other, means on an inner one of said concentric members to attach one end thereof to said syringe body and means on the other end thereof to attach said inner one of said concentric members to said needle, and means on an outer one of said concentric members to lock said outer concentric member in an extended position covering a needle, wherein said outer concentric member comprises a series of tangs, slots between said tangs and a flange at one end of each of said tangs.

2. The attachment of claim 1 further comprising a groove on the outer wall of said inner concentric member, and wherein said means to lock comprises a flange engaging said groove.

3. The attachment of claim 1 further comprising an annular ridge on the outside of said outer concentric member.

4. The attachment of claim 1 further comprising a capillary in said inner concentric member to establish fluid communication between said needle and said syringe body.

5. The attachment of claim 1 wherein said means to lock comprises a groove on said inner concentric member engaging said flanges when said outer member is in an extended position.

6. The attachment of claim 1 further comprising a slot extending axially on the outer wall of said inner concentric member and wherein a flange rides in said slot.

7. A syringe comprising: a syringe body, a needle, a connector between said syringe body and said needle, said connector comprising a first member to establish fluid communication between said needle and said syringe body and a second member slidable on said first member to cover said needle, wherein said second member comprises a series of tangs, slots between said tangs and a flange at one end of each of said tangs.

8. The syringe of claim 7 wherein said second member includes an annular ridge on an outside wall thereof.

9. The syringe of claim 7 wherein said first member includes an annular groove and said second member includes an inwardly extending flange engaging said groove to lock said second member in an extended position over said needle.

10. The syringe of claim 7 wherein said first and second members are concentric tubular members.

11. The syringe of claim 7 wherein said means to lock comprises a groove on said first member engaging said flanges when said second member is in an extended position.

12. The syringe of claim 7 further comprising a slot extending axially on said first member and wherein a flange rides in said slot.

* * * * *